(12) United States Patent
Krasowski et al.

(10) Patent No.: US 10,977,776 B1
(45) Date of Patent: Apr. 13, 2021

(54) TWO AND THREE-DIMENSIONAL NEAR INFRARED SUBCUTANEOUS STRUCTURE IMAGER USING REALTIME NONLINEAR VIDEO PROCESSING

(71) Applicant: United States of Americas as represented by the Administrator of NASA, Washington, DC (US)

(72) Inventors: Michael J. Krasowski, Chagrin Falls, OH (US); Joseph M. Flatico, Lakewood, OH (US); Phillip P. Jenkins, Cleveland, OH (US); Lawrence C. Greer, Avon, OH (US)

(73) Assignee: United States of America as Represented by the Administrator of National Aeronautics and Space Administration, Washington, DC (US)

( * ) Notice: Subject to any disclaimer, the term of this patent is extended or adjusted under 35 U.S.C. 154(b) by 366 days.

(21) Appl. No.: 16/056,713

(22) Filed: Aug. 7, 2018

Related U.S. Application Data

(63) Continuation-in-part of application No. 12/285,157, filed on Sep. 30, 2008, now Pat. No. 10,062,356.

(51) Int. Cl.
| | |
|---|---|
| *G06T 5/00* | (2006.01) |
| *H04N 5/243* | (2006.01) |
| *A61B 5/00* | (2006.01) |
| *A61B 5/103* | (2006.01) |
| *H04N 5/232* | (2006.01) |
| *G06T 5/50* | (2006.01) |

(52) U.S. Cl.
CPC .............. *G06T 5/008* (2013.01); *A61B 5/489* (2013.01); *G06T 5/50* (2013.01); *H04N 5/23216* (2013.01); *H04N 5/23229* (2013.01); *H04N 5/243* (2013.01); *A61B 2576/02* (2013.01); *G06T 2207/10016* (2013.01); *G06T 2207/10048* (2013.01); *G06T 2207/20192* (2013.01); *G06T 2207/20224* (2013.01); *G06T 2207/30101* (2013.01)

(58) Field of Classification Search
None
See application file for complete search history.

(56) References Cited

U.S. PATENT DOCUMENTS

| | | | | |
|---|---|---|---|---|
| 4,817,622 A | * | 4/1989 | Pennypacker | ....... A61B 5/0059 250/330 |
| 4,980,756 A | | 12/1990 | Lagoni | |
| 6,122,042 A | | 9/2000 | Wunderman et al. | |

(Continued)

*Primary Examiner* — David P Porta
*Assistant Examiner* — Carolyn Fin
(74) *Attorney, Agent, or Firm* — Robert H. Earp, III; Mark Wolfgang; Helen M. Galus

(57) ABSTRACT

A method includes placing an imaging device in contact with a sample, irradiating the sample via an illuminator such that radiation scatters off of the structure, and providing the scattered radiation to a detector to generate a digital video signal. A processor then performs various operations including subtracting a sum of a black state value and a user-defined black level clamping value from the digital video signal to create subtracted image data, substituting negative values in the subtracted image data with a reference value to create modified image data, and amplifying the modified image data by a user-defined gain to create contrast enhanced image data.

20 Claims, 7 Drawing Sheets

(56) References Cited

U.S. PATENT DOCUMENTS

| | | | |
|---|---|---|---|
| 2007/0038118 A1* | 2/2007 | Depue | A61B 5/489 600/476 |
| 2008/0122857 A1* | 5/2008 | Hsuan | G06T 5/009 345/589 |
| 2008/0147147 A1 | 6/2008 | Griffiths et al. | |

* cited by examiner

TWO AND THREE-DIMENSIONAL NEAR INFRARED SUBCUTANEOUS STRUCTURE IMAGER USING REALTIME NONLINEAR VIDEO PROCESSING

CROSS REFERENCE TO RELATED APPLICATION

This application is a continuation-in-part of, and claims priority to, co-pending U.S. patent applicant Ser. No. 12/285,157 entitled "TWO AND THREE DIMENSIONAL NEAR INFRARED SUBCUTANEOUS STRUCTURE IMAGER USING REALTIME NONLINEAR VIDEO PROCESSING," filed on Sep. 30, 2008. The subject matter of this earlier-filed application is hereby incorporated by reference in its entirety.

The present disclosure is also made in the performance of work under a NASA contract and is subject to the provisions of Section 305 of the National Aeronautics and Space Act, Public Law 111-314, § 3 (124 Stat. 3330, 51 U.S.C. Chapter 201).

ORIGIN OF DISCLOSURE

The present disclosure is based on work performed by employees of the United States Government and may be manufactured and used by or for the Government for Government purposes without the payment of any royalties thereon or therefore.

TECHNICAL FIELD

The present invention relates generally to imaging systems, and particularly near-infrared imaging systems.

BACKGROUND

In a clinical setting, the locating of subcutaneous structures, such as veins, for needle insertion can often be problematic. For example, small veins in pediatric patients, or veins in very dark-skinned or obese people, can be difficult to see or palpate. In emergency situations, such as accident sites, or battlefield situations, the need to locate a subcutaneous vessel, or a vessel exposed in a wound site, can arise unexpectedly. Thus, under-skilled persons may be called upon to access a subcutaneous vessel, for example, to insert a needle, or to tie off a bleeder. Thus, an imager that allows a user to view the subcutaneous vessel is needed.

Present subcutaneous vessel imagers use large, multiple, and often separate assemblies with complicated optics to image subcutaneous structures as two-dimensional maps on a wide monitor, or as maps extracted by a computer and focused onto the skin by a video projection. Furthermore, due to the scattering of the infrared light, veins imaged by prior art methods appear shadowy and distorted. Thus, an imager which allows a user to view subcutaneous structures and produce two-dimensional or three-dimensional images, yet which is still compact and inexpensive, is needed

SUMMARY

One embodiment provides a method of imaging a structure within a sample. The method includes placing an imaging device and an illuminator in proximity to the sample such that radiation originating from the illuminator has a propagation path to a surface of the sample. The method also includes irradiating the sample via the illuminator such that at least a portion of the radiation scatters off of the structure. The method also includes providing the scattered radiation to a detector to generate a digital video signal. The method also includes determining, via a processor communicably coupled to the imaging device, a black state value for the digital video signal. The method also includes subtracting, via the processor, a sum of the black state value and a user-defined black level clamp voltage from the digital video signal to create a subtracted digital video signal. The method also includes setting, via the processor, negative values in the subtracted digital video signal to a reference level to create modified image data. The method also includes amplifying, via the processor, the modified image data by a user-defined gain to create contrast enhanced image data. The method also includes displaying, via a display device, the contrast enhanced image data to provide an image of the structure.

Another embodiment relates to a method of imaging a structure within a sample. The method includes placing an imaging device in contact with the sample such that radiation originating from an illuminator of the imaging device has a propagation path to a surface of the sample. The method also includes irradiating the sample via the illuminator such that at least a portion of the radiation scatters off of the structure. The method also includes providing the scattered radiation to a detector to generate a digital video signal. The method also includes determining, via a processor communicably coupled to the imaging device, a black state value for the digital video signal. The method also includes subtracting, via the processor, a sum of the black state value and a user-defined black level clamping value from the digital video signal to create subtracted image data. The method also includes substituting, via the processor, negative values in the subtracted image data with a reference value to create modified image data. The method also includes amplifying, via the processor, the modified image data by a user-defined gain to create contrast enhanced image data. The method also includes displaying, via a display device, the contrast enhanced image data to provide an image of the structure.

BRIEF DESCRIPTION OF THE DRAWINGS

For proper understanding of the invention, reference should be made to the accompanying drawings, wherein.

DETAILED DESCRIPTION OF THE PREFERRED EMBODIMENT(S)

It will be readily understood that the components of the present invention, as generally described and illustrated in the figures herein, may be arranged and designed in a wide variety of different configurations. Thus, the following detailed description of the embodiments of an apparatus, a system, a method, and a computer readable medium, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, the usage of "certain embodiments," "some embodiments," or other similar language, throughout this specification refers to the fact that a particular feature, structure, or characteristic described in connection with the embodiment may be included in at least one embodiment of the present invention. Thus, appearances of the phrases "in certain embodiments," "in some embodiments," "in other embodiments," or other similar language, throughout this specification do not necessarily all refer to the same group of embodiments, and the described features, structures, or characteristics may be combined in any suitable manner in one or more embodiments.

An innovative near-infrared imager which provides a high contrast visualization of subcutaneous structures is described. Utilizing this innovative near-infrared imager, an operator can see subcutaneous structures with a sense of location and depth. This imager may operate in complete darkness and is not impeded by melanin in the skin. The imager may be useful for the locating of veins and other structures for access, such as needle insertion or excision. The imager can operate as either a two-dimensional imager or a three-dimensional imager.

The imager includes an adaptive nonlinear processor to increase image contrast. According to embodiments of the invention, video frames are passed through the processor which may drive dark levels before a certain threshold to a maximum black level. The processor may then adjust the gain for signals above this level to stretch the video to a maximum white level. This function may allow the user of the imager to make a subcutaneous structure (such as a vein) the darkest feature in the image, while stretching the remaining gray levels toward the white.

Figure 1:
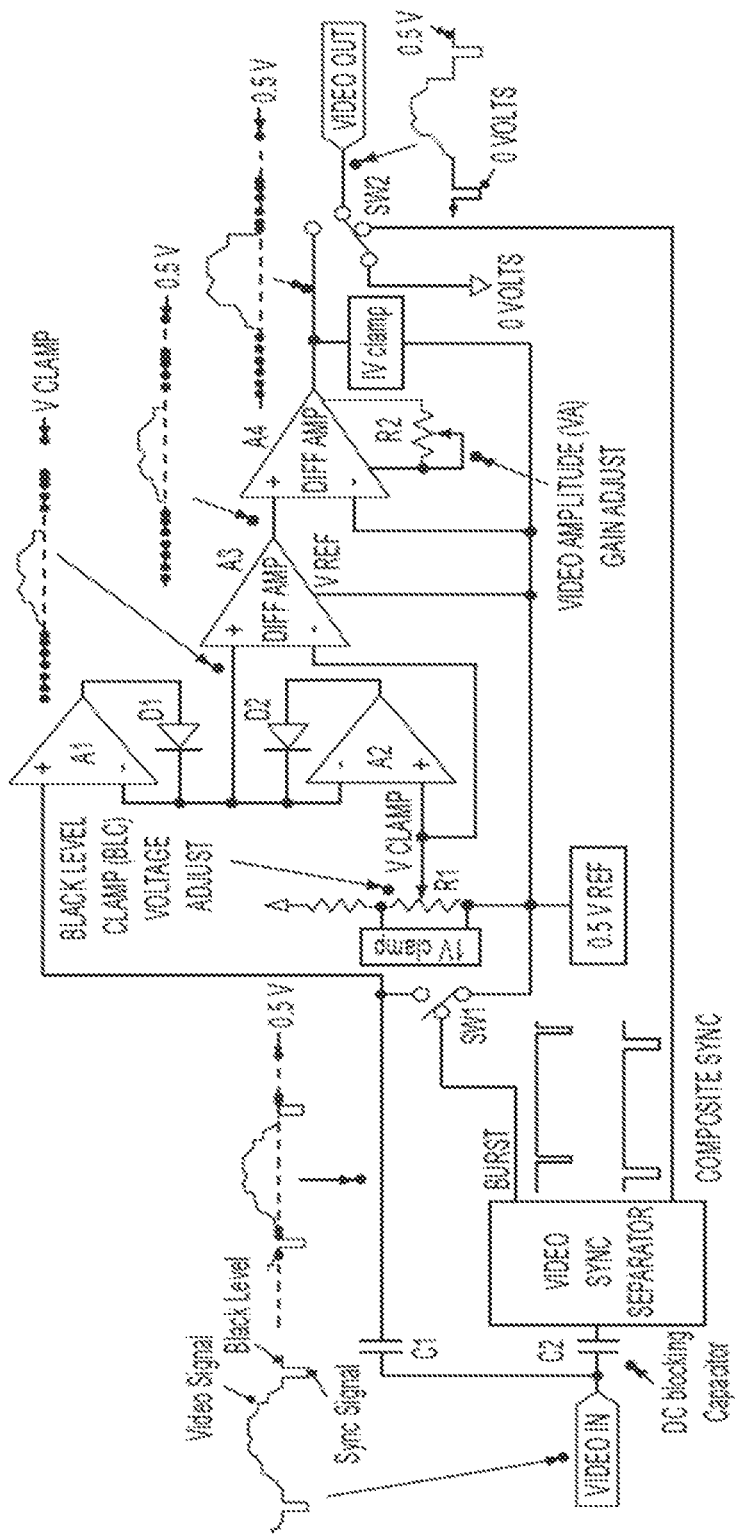
FIG. 1 illustrates an example embodiment of an adaptive nonlinear processor according to an embodiment of the present invention.

FIG. 1 is a block diagram which illustrates an example embodiment of an adaptive nonlinear processor, according to an embodiment of the present invention.

The depicted adaptive nonlinear processor may include a video in component, which receives a video signal. The video signal may be any type of composite video (for example RS-170). Composite video is a format of an analog video signal. Composite video is also referred to as "Color, Video, Blank and Sync" or CVBS. A composite video signal is a composite of three source signals called Y, U, and V (together referred to as YUV), and also includes synch pulses. A synch pulse is a negative-going timing pulse used to synchronize the horizontal and vertical portions of the display. A composite video signal is usually in a standard format such as National Television System Committee (NTSC), Phase Alternating Line (PAL), and Séquentiel Couleur à Mémoire (i.e. Sequential Color With Memory) (SECAM).

A portion of a composite video signal that makes up one horizontal scan line of a picture includes an active video portion and a horizontal blanking portion.

The horizontal blanking portion includes a front porch portion, a sync tip portion, a breezeway portion, a color burst portion, and a black porch portion. The front porch is the beginning of the composite video signal (or the area which occurs right after the end of the active video portion) and occurs before the leading edge of the synch pulse. The sync tip is the area of the composite video signal which includes the synch pulse. The breezeway is the area of the composite video signal defined as the time between the rising edge of the sync pulse and the start of the color burst. The color burst, also known as the color subcarrier, is 8 to 10 cycles of a color reference frequency. It is positioned between the rising edge of the sync pulse, and the start of the active video portion of the composite video signal. Finally the back porch is the area of the composite video signal between the end of the color burst and the start of the active video portion.

The active video portion contains the picture brightness (luma) and color (chroma) information. The brightness information is the instantaneous amplitude at any point in time. Color information is added on top of the luma signal and is a sine wave with the colors identified by a specific phase difference between it and a color burst reference phase. An amplitude of the modulation is proportional to the amount of color (or saturation), and the phase information denotes the tint (or hue) of the color.

In certain embodiments of the invention, the video signal of FIG. 1 may have embedded synchronization pulses, as well as a black level at a back porch. In certain embodiments, the video signal has the following values:
White: +1.000 V
Black: +0.075 V
Blank: 0 V
Sync: −0.400 V The depicted adaptive nonlinear processor may include DC-blocking capacitors C1 and C2, and a video sync separator circuit, video sync separator. C1 and C2 block the DC component of the video signal, creating one path through C2 to the video sync separator, and one path through C1 to the video circuitry. The video sync separator circuit creates a pulse train, identified in FIG. 1 as composite sync, which is coincident to the position of the horizontal and vertical sync pulses, and another pulse train, identified in FIG. 1 as burst, which is coincident to the area on the back porch which is at the black level.

The depicted adaptive nonlinear processor may include switch SW1. According to the embodiment of the invention, after the video signal has passed through capacitor C1, its DC black level is clamped to the on circuit 0.5 volt reference voltage, identified in FIG. 1 as 0.5 V REF by shorting the circuit side of C1 to voltage 0.5 V REF through switch SW1 during the back porch portion of the video signal. Thus, 0.5 volts DC is stored on the circuit side of C2, and thus biases the video signal. Droop is minimal, as this voltage is refreshed after each and every sync pulse.

The resulting video signal now has its black level biased to 0.5 volts DC and is passed on to the maximum value circuit for black level clamping. A clamp is a circuit that forces a specific portion (either the back porch or the sync tip) of the video signal to a specific DC voltage, to restore the DC level. The black level clamp forces the back-porch voltage to be equal to the voltage produced by the potentiometer identified in FIG. 1 as black level clamp (BLC) voltage adjust.

The potentiometer, black level clamp (BLC) voltage adjust, produces a voltage, identified in FIG. 1 as v clamp. The voltage v clamp, rides above voltage 0.5 V REF, but is biased below some upper voltage such that the range of voltage v clamp is approximately 0.5 V REF to (1+0.5 V REF). This satisfies a full video white level of +1.000 V above Blank, as noted above.

The resulting video signal is also passed to a maximum value circuit. In the embodiment depicted in FIG. 1, the maximum value circuit is represented by amplifiers A1 and A2, and diodes D1 and D2. However, one of ordinary skill in the art would readily understand that this circuit topography is merely an example of the maximum value circuit, and that the maximum value circuit could be represented by other circuit topographies, in alternative embodiments, and be consistent with the invention. Thus, the circuit topography of the maximum value circuit is not limited to the circuit topography displayed in FIG. 1.

According to the embodiment of the invention, the amplifier A1 and the diode D1 handle the video signal, while the amplifier A2 and the diode D2 handle the voltage v clamp. Together, the output of the maximum value circuit, given as the node comprising the inverting inputs of both A1 and A2, and the diodes of D1 and D2, will be the maximum of the two inputs, the video signal and the voltage v clamp. For example, if the voltage v clamp is set to 0.8 volts above voltage 0.5 V REF, then all video signal components below 0.8 volts above voltage 0.5 V REF will be suppressed, and the output of this maximum value circuit shall be 0.8 volts. If any components of the incoming video signal are above 0.8 volts above voltage 0.5 V REF, then the output of this maximum value circuit shall be the values of that incoming video signal exceeding 0.8 volts over voltage 0.5 V REF. Thus, setting voltage v clamp also sets where the useable incoming video signal shall start.

The depicted adaptive nonlinear processor may also include a unit gain difference amplifier. The difference amplifier is identified in FIG. 1 as amplifier A3. However, one of ordinary skill in the art would readily understand that this circuit topography is merely an example of the unit gain difference amplifier, and that the unit gain difference amplifier could be represented by other circuit topographies, in alternative embodiments, and be consistent with the invention. Thus, the circuit topography of the unit gain difference amplifier is not limited to the circuit topography displayed in FIG. 1.

According to the embodiment of the invention, the reference of amplifier A3 is voltage 0.5 V REF. The output of the maximum value circuit is routed to the positive input of amplifier A3, while voltage v clamp is routed to its negative input. Thus, the output of this amplifier is the output of the maximum value circuit minus voltage v clamp, referenced to voltage 0.5 V REF. In other words, the output of amplifier A3 is voltage 0.5 V REF, plus the output of the maximum value circuit minus voltage v clamp. Thus, the output of amplifier A3 is the video signal where all the amplitude components are above voltage v clamp, and riding atop of voltage 0.5 V REF.

Thus, according to the embodiment of the invention, the contrast of the video signal may be adjusted. Specifically, the black level of the video signal may be adjusted.

The depicted adaptive nonlinear processor may also include a variable gain difference amplifier. The difference amplifier is identified in FIG. 1 as amplifier A4. However, one of ordinary skill in the art would readily understand that this circuit topography is merely an example of the variable gain difference amplifier, and that the variable gain difference amplifier could be represented by other circuit topographies, in alternative embodiments, and be consistent with the invention. Thus, the circuit topography of the variable gain difference amplifier is not limited to the circuit topography displayed in FIG. 1.

According to the embodiment of the invention, the lowest possible gain of amplifier A4 is unity, and the upper gain limit of amplifier A4 is sufficient to stretch the video signal after clamp and maximum value processing up to BLANK plus+1.000 volts. The output of amplifier A4 is clamped such that if the output of amplifier A4 attempts to exceed BLANK plus+1.000 volts, its output is clamped to BLANK plus+1.000 volts. This is done to stay within specifications for video standards, and not stress display devices. Thus, as an example, if after clamp and maximum value processing, the maximum video amplitude component is BLANK plus 0.5 volts, and a user desires more brightness, the user may adjust the gain of amplifier A4 towards a value of two to move the resulting video signal amplitude component toward BLANK plus+1.000 volts. This adjustment to the gain value is done by a potentiometer, identified in FIG. 1 as video amplitude (VA) gain adjust. Since the negative input of amplifier A4 is based on voltage 0.5 V REF, the resulting signal is the amplified version of the output of amplifier A3, also referenced to voltage 0.5 V REF.

The depicted adaptive nonlinear processor may include switch SW2. SW2 is a single pole dual throw switch, whose position is controlled by composite sync. When composite sync is high, signifying blank, black, or video, the video signal output from amplifier A4 is passed onto the display device, biased to voltage 0.5 V REF. When composite sync is low, signifying the presence of a sync pulse, the switch is controlled to pass 0 volts. Thus, the outgoing video signal has sync tips that are consistent with Sync: −0.400 V.

Thus, according to the embodiment of the invention, the depicted adaptive nonlinear processor may adjust the contrast of the video signal by clamping the video signal so that the black levels below a first threshold appear black when displayed. Furthermore, according to the embodiment of the invention, the depicted adaptive nonlinear processor may further adjust the contrast of the video signal by adjusting the gain of the video signal so that the resulting gray levels above a second threshold are stretched to white, so that the resulting gray levels appear whiter when displayed. Accordingly, the depicted adaptive nonlinear processor may adjust the incoming video signal's contrast and brightness to create a nonlinear transfer function which produces and image wherein the feature of choice, for example, the subcutaneous structure, may be presented maximally contrasted against background brightness.

According to certain embodiments of the invention, the first and second thresholds may be automatically established by the imager. However, in alternative embodiments of the invention, the thresholds may be established by the user. Furthermore, in alternatives embodiments of the invention, the user may adjust the thresholds to further adjust the contrast of the displayed image.

In the embodiment of the invention depicted in FIG. 1, the adaptive nonlinear processor may have one breakpoint for the piecewise linear approximation to a nonlinear transfer function to adjust the contrast and the brightness of the incoming video signal. However, in alternative embodiments, more breakpoints may be easily added through replication of the maximum value circuit and gain circuits shown in FIG. 1 to create a piecewise linear approximation to any desired nonlinear transfer function. These breakpoints may be manipulated manually, manipulated automatically, fixed, or any combination of the three.

As described above, the adaptive nonlinear processor of the invention may be utilized in various embodiments of the imager. Exemplary embodiments of the imager are described below in more detail.

Figure 2:
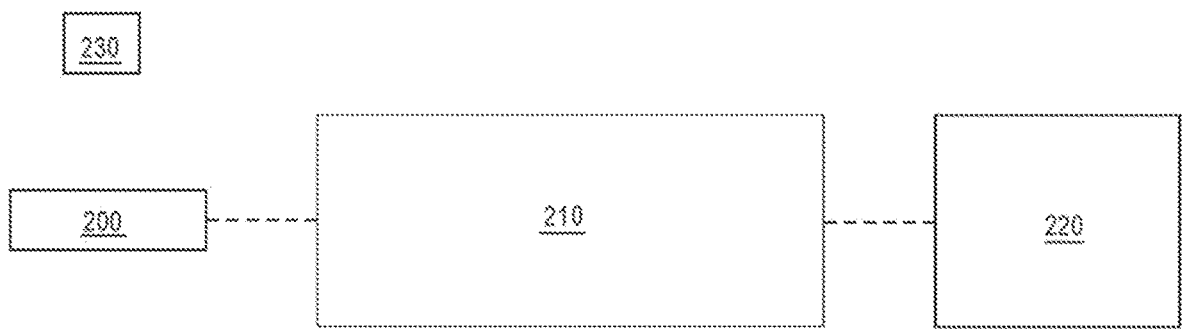
FIG. 2 illustrates another example embodiment of an imager according to an embodiment of the present invention.

FIG. 2 illustrates an example embodiment of an imager which utilizes an adaptive nonlinear processor according to the present invention. The imager includes camera 200, adaptive nonlinear processor 210, and display 220. Camera 200 may be configured to produce a video signal. The adaptive nonlinear processor 210 may be configured to receive the video signal from the camera 200, and to process the video signal by adjusting the contrast of the video signal, as described in relation to the adaptive nonlinear processor of FIG. 1. In certain embodiments, the adaptive nonlinear processor 210 corresponds to an adaptive nonlinear processor as depicted in FIG. 1. The display 220 may be configured to display the video signal which is output by the adaptive nonlinear processor 210.

In this exemplary embodiment, the adaptive nonlinear processor 210 may receives the video frame from one camera. Thus display 220 may display a two-dimensional image of a subcutaneous structure for the user. In certain embodiments, the adaptive nonlinear processor 210 may be embedded within the camera 200.

Furthermore, according to certain embodiments, camera 200 may include a low-power complementary metal oxide semiconductor (CMOS) single-chip imager. Camera 200 may also include an optical lens and a filter according to certain embodiments. The optical lens and filter of each camera may be optimized for near-infrared light with a wavelength range of 940 to 950 nanometers.

In certain embodiments, the camera 200 is a NTSC camera, which is configured to output a NTSC composite video signal. However, one of ordinary skill in the art would readily understand that the processor may work with any type of camera, and may work with any format of composite video (such as PAL, and SECAM).

According to the embodiment of the invention, the display 220 of the imager may be any display which accepts NTSC video signals. According to certain embodiments, the display 220 of the imager may be a virtual reality headset. In certain embodiments, camera 220 is affixed to an adjustable binocular assembly mounted to the front of the virtual reality headset display. The virtual reality headset display may display a two-dimensional image produced by camera 200 and adaptive nonlinear processor 210.

According to certain embodiments, the imager may include an illuminator 230. The illuminator is configured to illuminate the site that camera 200 is viewing. In certain embodiments, the illuminator may be mounted to camera 200. However, one of ordinary skill in the art would readily understand that in alternative embodiments, the illuminator 230 may be a separate, stand-alone component. Furthermore, one of ordinary skill in the art would readily understand that the imager may function using natural light, without the aid of an illuminator. Thus, while the embodiment of the imager depicted in FIG. 2 includes an illuminator, in other alternative embodiments of the invention, the imager may not include an illuminator.

The use of illuminator 230 may allow the imager to penetrate the skin and view subcutaneous structures in greater detail. In certain embodiments, illuminator 230 may include, for example, one or more of infrared light-emitting diodes. Infrared light may be useful in penetrating the skin and viewing the subcutaneous structure. In alternative embodiments, illuminator 230 may comprise a quartz halogen lamp. A quart halogen lamp is also very rich in near infrared-light, and may allow subcutaneous structures to stand out, with the subcutaneous structure appearing very black in contrast to the skin, which appears very white.

Furthermore, in certain embodiments, the illuminator 230 may be configured to emit near-infrared light with a wavelength of a range from 940 to 950 nanometers. A wavelength of a range from 940 to 950 nanometers may be optimal, since the wavelength penetrates the skin well, melanin at that wavelength, the CMOS imager of the camera 200 is very sensitive at that wavelength, and that certain types of blood (such as blood with reduced hemoglobin values) absorbs light strongly at that wavelength.

According to the embodiment depicted in FIG. 2, camera 200, adaptive nonlinear processor 210, and display 220 may be separate components, which may be operatively connected. However, one of ordinary skill in the art would readily understand that in alternative embodiments, camera 200, adaptive nonlinear processor 210, and display 220 may be physically connected as an integrated structure. For example, a portable handheld, battered powered device with an embedded illuminator, camera and display is consistent with the spirit and scope of the invention.

Figure 3:
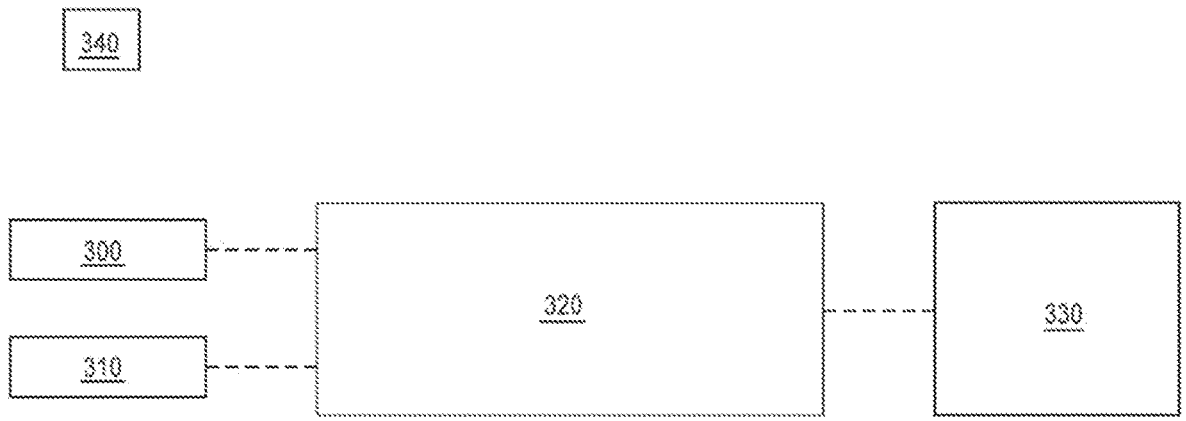
FIG. 3 illustrates another example embodiment of an imager according to an embodiment of the present invention.

FIG. 3 illustrates an example embodiment of an imager which utilizes an adaptive nonlinear processor according to the present invention. In this exemplary embodiment, the imager includes a first camera 300 and a second camera 310. Cameras 300 and 310 may each be configured to produce a video signal. According to certain embodiments of the invention, cameras 300 and 310 may each correspond to camera 200 as depicted in FIG. 2.

The imager also includes an adaptive nonlinear processor 320. The adaptive nonlinear processor 320 may be configured to receive the video signal from the cameras 300 and 310, and to process the video signal by adjusting the contrast of the video signal, as described in relation to the adaptive nonlinear processor of FIG. 1. In certain embodiments, the adaptive nonlinear processor 320 corresponds to an adaptive nonlinear processor as depicted in FIG. 1. The imager also includes a display 330 configured to display the video signal which is output by the adaptive nonlinear processor 320.

Because the embodiment of the invention depicted in FIG. 3 includes two cameras, as opposed to one camera as shown in the embodiment of the invention depicted in FIG. 2, the manner in which the cameras 300 and 310 provide the video signal may be utilized to produce a three-dimensional image of a subcutaneous structure.

The manner in which cameras 300 and 310 may provide the video signal to the adaptive nonlinear processor 320 will now be discussed in more detail, according to an embodiment of the invention. A NTSC camera normally produces an odd and even field of a video frame. A standard NTSC video signal is divided into odd and even fields every $\frac{1}{60}$th of a second, with the second field interlaced or vertically offset between the scan lines of the first, to produce a complete image every $\frac{1}{30}$th of a second. An identity of the field tells the monitor, camera, or other video device, whether the current field contains the odd or even scan lines. This is known as generation locking or genlocking.

According to certain embodiments of the invention, the genlocking of two images with odd/even field multiplexing is replaced with left/right camera multiplexing, so that cameras 300 and 310 both produce their even field at the same time, and both produce their odd field at the same time.

Thus, according to certain embodiments of the invention, cameras 300 and 310 may be multiplexed such that first camera 300 and second camera 310 each supply a separate field of the video frame to the adaptive nonlinear processor 320. This ultimately produces a stereoscopic image which can be displayed by display 330. The stereoscopic image may produce a three-dimensional image to the user who views display 230.

According to certain embodiments of the invention, display 330 may correspond to display 200 as depicted in FIG. 2. Furthermore, according to certain embodiments, the display 330 of the imager may be a virtual reality headset. In certain embodiments, cameras 300 and 310 are affixed to an adjustable binocular assembly mounted to the front of the virtual reality headset display. The virtual reality headset display is configured to display the fields from first camera 300 to the left eye of a user and those from second camera 310 to the right eye of the user. Thus, the virtual reality headset display may display a three-dimensional image based on the stereoscopic image produced by the multiplexing of cameras 300 and 310.

According to certain embodiments, the imager may include an illuminator 340 According to certain embodiments of the invention, illuminator 340 may correspond to illuminator 230 as depicted in FIG. 2.

According to the embodiment depicted in FIG. 2, cameras 300 and 310, adaptive nonlinear processor 320, and display 330 may be separate components, which may be operatively connected. However, one of ordinary skill in the art would readily understand that in alternative embodiments, cameras 300 and 310, adaptive nonlinear processor 320, and display 330 may be physically connected as an integrated structure.

Figure 4:
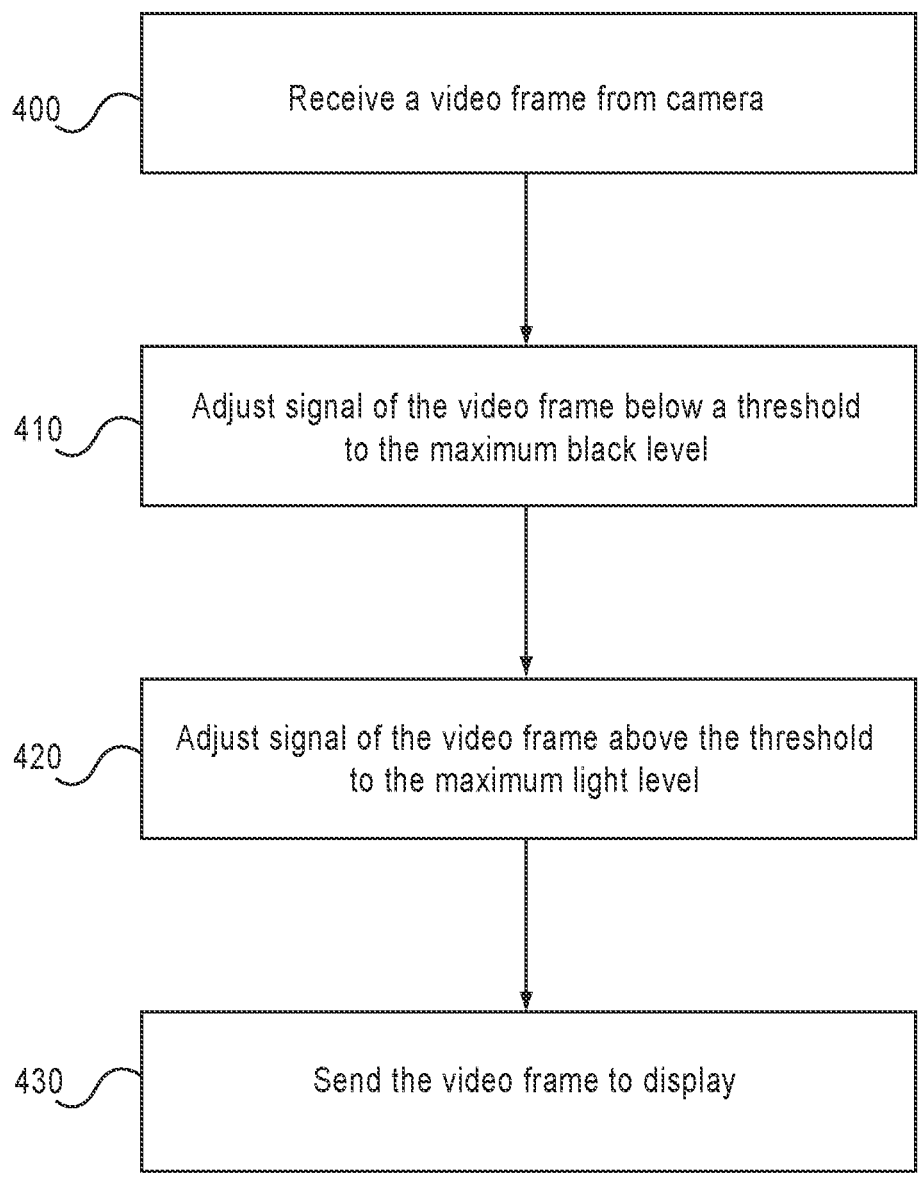
FIG. 4 illustrates a method, in accordance with another embodiment of the present invention.

FIG. 4 is a method for generating an image of a subcutaneous structure, in accordance with an embodiment of the invention. At step 400, a video frame is received from a camera configured to generate the video frame. At step 410, the signal of the video frame is adjusted below a threshold to a maximum dark level. At step 420, the signal of the video frame is adjusted above the threshold to a maximum light level. At step 430, the video frame is sent to a display configured to display the video frame. Thus, according to the embodiment of the invention, the method may produce a two-dimensional image of a subcutaneous structure.

Figure 5:
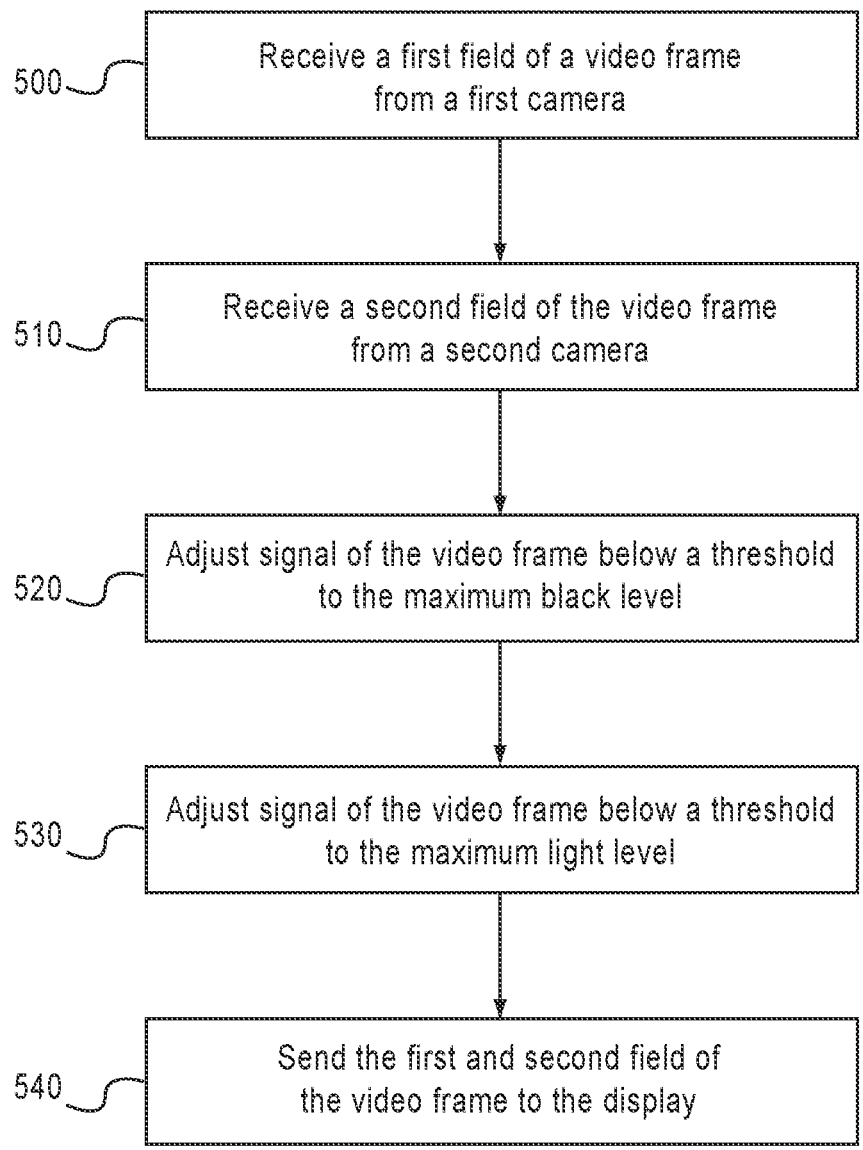
FIG. 5 illustrates another method, in accordance with another embodiment of the present invention.

FIG. 5 is a method for generating an image of a subcutaneous structure, in accordance with another embodiment of the invention. At step 500, a first field of a video frame is received from a first camera. At step 510, a second field of a video frame is received from a second camera. At step 520, a signal of the video frame is adjusted below a threshold to a maximum dark level. At step 530, the signal of the video frame is adjusted above the threshold to a maximum light level. At step 540, the video frame is sent to a display configured to display the first field of the video frame and the second field of the video frame. Thus, according to the embodiment of the invention, the method may produce a three-dimensional image of a subcutaneous structure.

The method steps performed in FIG. 4 and FIG. 5 may be performed by a computer program product, encoding instructions for the nonlinear adaptive processor to perform at least the method described in FIG. 4 and the method described in FIG. 5, in accordance with an embodiment of the present invention. The computer program product may be embodied on a computer readable medium. A computer readable medium may be, but is not limited to, a hard disk drive, a flash device, a random access memory, a tape, or any other such medium used to store data. The computer program product may include encoded instructions for controlling the nonlinear adaptive processor to implement the method described in FIG. 4, and the method described in FIG. 5, which may also be stored on the computer readable medium.

Figure 6:
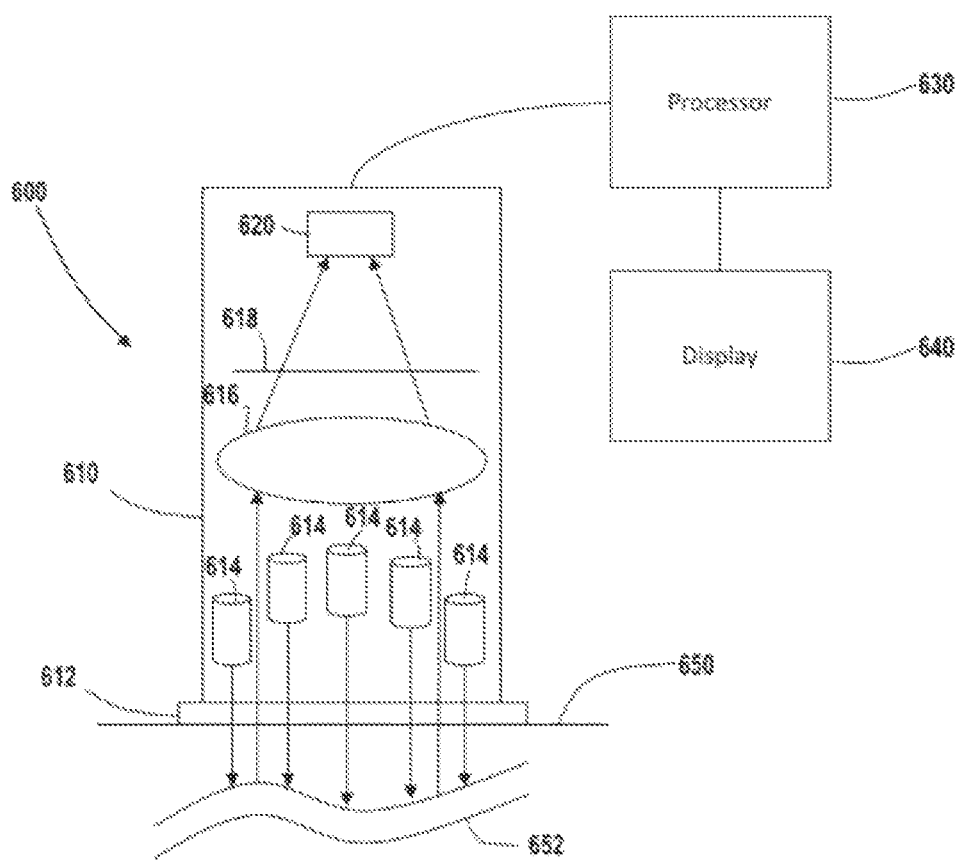
FIG. 6 illustrates another example embodiment of an imager according to an embodiment of the present invention.

Referring now to FIG. 6, an imaging system 600 is shown, according to an example embodiment. The imaging system 600 includes an imaging device 610, a processor 630, and a display 640. The imaging device 610 includes various components configured to provide radiation to a sample 650. In the example shown, the imaging device 610 includes an optically transparent material 612 at an end thereof. The optically transparent material 612 is generally a material that minimally absorbs light within the bandwidth (e.g., between 750 nm and 1000 nm) of an illumination source (e.g., the light sources 614) of the imaging device 610.

The optically transparent material 612 is configured to be placed in contact with the sample 650 including a structure to be imaged 652 (e.g., a vein or other blood vessel). The contact between the optically transparent material 612 and the sample 650 diminishes the length of a propagation path between the imaging device 610 and the sample 650. Such a propagation path reduces noise in a resultant image signal by curtailing the scattering of light from a surface of the sample 650 that would take place if the imaging device 610 were not pressed against the sample 650. In certain embodiments, the optically transparent material 612 includes a lens configured to render the imaging device 610 telecentric. In some embodiments, additional material such as an index matching material, a liquid, and/or a gel, is placed between the optically transparent material to further reduce scattering at the surface of the sample 650.

As shown, the imaging device 610 includes light sources 614, a focusing device 616, an optical filter 618, and a detector 620. Light sources 614 are disposed between the focusing device 616 and the optically transparent material 612. In the example shown, light sources 614 are identical and arranged in a ring centered about a central axis of the imaging device 610. In various embodiments, light sources 614 are light emitting diodes configured to emit near infrared light. The particular emission band of the light sources 614 may be fixed or adjustable and vary depending on the implementation. For example, wavelengths between 820 nm and 950 nm may be used to image veins, as this range is absorbed by venous blood with the longer wavelengths in this range being well suited to pass through fat tissue. Other emission bands may be used depending on a desired structure to be imaged 652. Additionally, certain ones of the light sources 614 may have different emission bands than others in some embodiments (and such emission bands may be independently adjustable via user manipulation, as described herein). The ring-shaped arrangement of the light sources 614 is beneficial in that it illuminates a relatively wide area of the sample 650. It should be understood that alternative arrangements of the light sources 614 is envisioned.

In some embodiments, the focusing device 616 includes an optical element configured to focus scattered light onto the detector 620. As shown, the focusing device 616 is a fixed convex lens configured to focus radiation scattered from the structure to be imaged 652 that passes through the light sources 614. The detector 620 is separated from the lens by approximately lens's focal length to provide quality resolution of the images generated thereby. In some embodiments, the focusing device 616 is adjustable through user manipulation of an input device (e.g., a knob or via connection to an external computing device). For example, the axial position of the lens shown in FIG. 6 may be adjusted to manipulate the focusing of the imaging device 610. The detector 620 is a two-dimensional imaging array (e.g., CCD detector) configured to generate a plurality of imaging signals from the light scattered from the structure to be imaged 652. From the plurality of imaging signals, a video signal to be processed by the processor 630 may be generated.

An optical filter 618 (e.g., a bandpass filter for a sub-band of the near infrared) is disposed between the focusing device 616 and the detector 620. The filter 618 is configured to block undesired wavelengths contained in the emission bands of the light sources 614. In various embodiments, the optical filter 618 may be left out or placed in any location between the optically transparent material 612 and the detector 620.

In the example shown, the imaging device 610 is a substantially cylindrical-shaped wand. For example, the imaging device 610 may include a housing of a suitable material that defines a volume within which the light sources 614, focusing device 616, optical filter 618, and detector 620 are disposed. The housing may include various structures configured to hold these respective components in a suitable arrangement for optical imaging performance. The imaging device 610 is a handheld device configured to be manipulated by a user (e.g., a healthcare provider) to contact the sample 650 (e.g., a patent) via the optically transparent material 612. The imaging device 610 may take various alternative shapes and forms (e.g., a stationary device mounted to a fixture) depending on the implementation.

As shown, the imaging device 610 is connected to a processor 630 and a display 640. It should be appreciated that the imaging device 610 may be connected to the processor 630 and display 640 in any suitable manner (e.g., via any wired or wireless connection). For example, in some embodiments, the display 640, processor 630, or both are mounted onto the imaging device 610 such that the imaging system 600 is a compact instrument. In other embodiments, the processor 630 and display 640 are separate from the imaging device 610.

The processor 630 is configured to receive the plurality of imaging signals generated via the detector 620 and perform various operations thereon to enhance the video signal to provide a view of the structure to be imaged 652 via the display 640. For example, in some embodiments, the processor 630 performs the operations described with respect to the adaptive nonlinear processor of FIG. 1. In certain embodiments, the processor 630 is a component (e.g. a microprocessor) of a computing system. The computing system may include a memory storing executable instructions configured to cause the processor 630 to perform the operations described herein on a video signal via a software implementation.

In various embodiments, the processor 630 includes a user interface device configured to receive various inputs from the user. The user interface device may include any number of electrical and mechanical components to enable the user to control various aspects of the processor 630's operation. For example, in one embodiment, the user interface device is a display (e.g., the display 640) configured to receive various user inputs. Through such a display, the user may manipulate various factors (e.g., clamp voltage, gain, etc.) impacting operations of the processor 630. In some embodiments, the user interface device includes various mechanical components (e.g., knobs) enabling the user to adjust such factors.

In some embodiments, the processor 630 is connected to the light sources 614 (or other illuminators in alternative implementations) and the user may manipulate the operations of the light sources through manipulation of the user interface device. For example, the light sources 614 may be tunable and possess input-dependent emission bands. The user may select emission bands for all or a subset of the light sources 614 via providing an input to the user interface. In certain embodiments, the user may turn the light sources 614 on and off by such an input. The processor 630 may also be connected to the focusing device 616 to enable user manipulation of the focusing of the imaging device 630 via user manipulation of the user input device.

In certain embodiments, the processor 630 (or a computing system incorporating the processor 630) may have various additional image processing capabilities including, but not limited to edge detection, edge enhancement, pseudo-coloring, histogram manipulation, manipulation of brightness, linear or non-linear filtering, addition or subtraction of multiple images, etc. These capabilities may take the form of microprocessor-executable instructions sets performed automatically or on demand by the processor 630. For example, in certain embodiments, the user may select a set of image processing techniques to apply to a particular video signal (e.g., after the processor 630 performs the contrast enhancement process described with respect to FIG. 1) via manipulation of the user input device.

Figure 7:
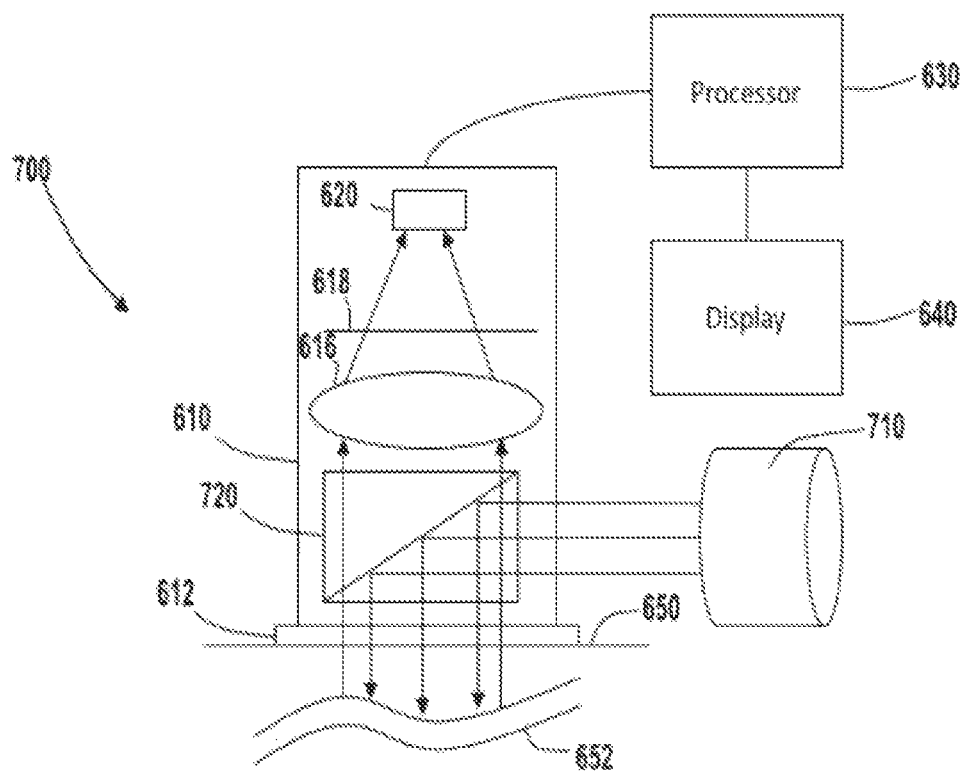
FIG. 7 illustrates another example embodiment of an imager according to an embodiment of the present invention.

Referring now to FIG. 7, an imaging system 700 is shown, according to an example embodiment. Imaging system 700 incorporates various components of the imaging system 600 described with respect to FIG. 6 and includes like reference numerals where appropriate. The imaging system 700 differs from the imaging system 600 in the illumination source. In contrast to the imaging system 600, in the imaging system 700, the imaging device 610 includes a light source 710 not disposed on the central axis of the imaging device 610. For example, the light source 710 may be attached to an external housing of the imaging device 610. The housing may include an optically transparent window on the side thereof to enable light from the light source 710 to reach a beam splitter 720 disposed on a central axis of the imaging device 610.

All or a portion of the radiation emitted from the light source 710 may reflect off a surface of the beam splitter 720 to travel towards the sample 650, which scatters radiation via the structure to be imaged 652. A portion of the scattered light transmits through the beam splitter 720 and is focused via the focusing device 616 onto the detector 620 to generate a video signal. In the shown embodiment, an additional optical element such as a lens may be incorporated between the optically transparent material 612 and the beam splitter 612 to render the imaging device 610 telecentric. In one embodiment, the additional optical element is disposed at (e.g., within) an opening at the end of the imaging device 610. The optically transparent material 612 may be disposed over the additional optical element in contact therewith. Alternatively, the additional optical element may replace the optically transparent material 612. Such embodiments are beneficial in that they provide a consistent illumination of the structure to be imaged 652 irrespective of that structure's position within the imaging device 610's field of view.

Certain embodiments may incorporate both the axial illumination source depicted in FIG. 6 and the non-axial illumination source depicted in FIG. 7. Each illumination source may be communicably coupled to the processor 630 enabling the user to select a suitable illumination method for a particular usage of the imaging device 610 via manipulation of the user input device attached thereto. Imaging devices may include any number of selectable illumination methods consistent with the present disclosure to provide maximum flexibility.

In certain implementations, imaging systems may incorporate multiple imaging devices 610 generating separate images from different angles of view. For example, the imaging devices 610 may be held in relation to one another via a mounting mechanism. In some embodiments, the relative positioning of the imaging devices 610 are adjustable via an embedded algorithm or user manipulation (e.g., via a user input device coupled to the processor 630). By adjusting the focusing of the imaging devices 610 and changing the angles of view, image reconstruction may be used from the plurality of video signals to generate three dimensional renderings.

Other implementations are envisioned where various elements of the imaging device 610 are incorporated into imaging systems including other modalities. For example, in some embodiments, an illumination source (e.g., light sources 614 or light source 710), focusing device 616, and detector 620 may disposed in a transducer body including an ultrasound imager to expand that imager's capabilities by providing near-infrared imaging. Alternatively, the imaging device 610 may be externally attached to an ultrasound imager such that the imaging device 610 and the transducer emit radiation out of a common surface. The imaging device 610 described herein may be similar in construction to existing ultrasound imagers. This makes these imaging modalities compatible with one another for simultaneous utilization, enabling healthcare provides to efficiently obtain multiple forms of diagnostic information.

Figure 8:
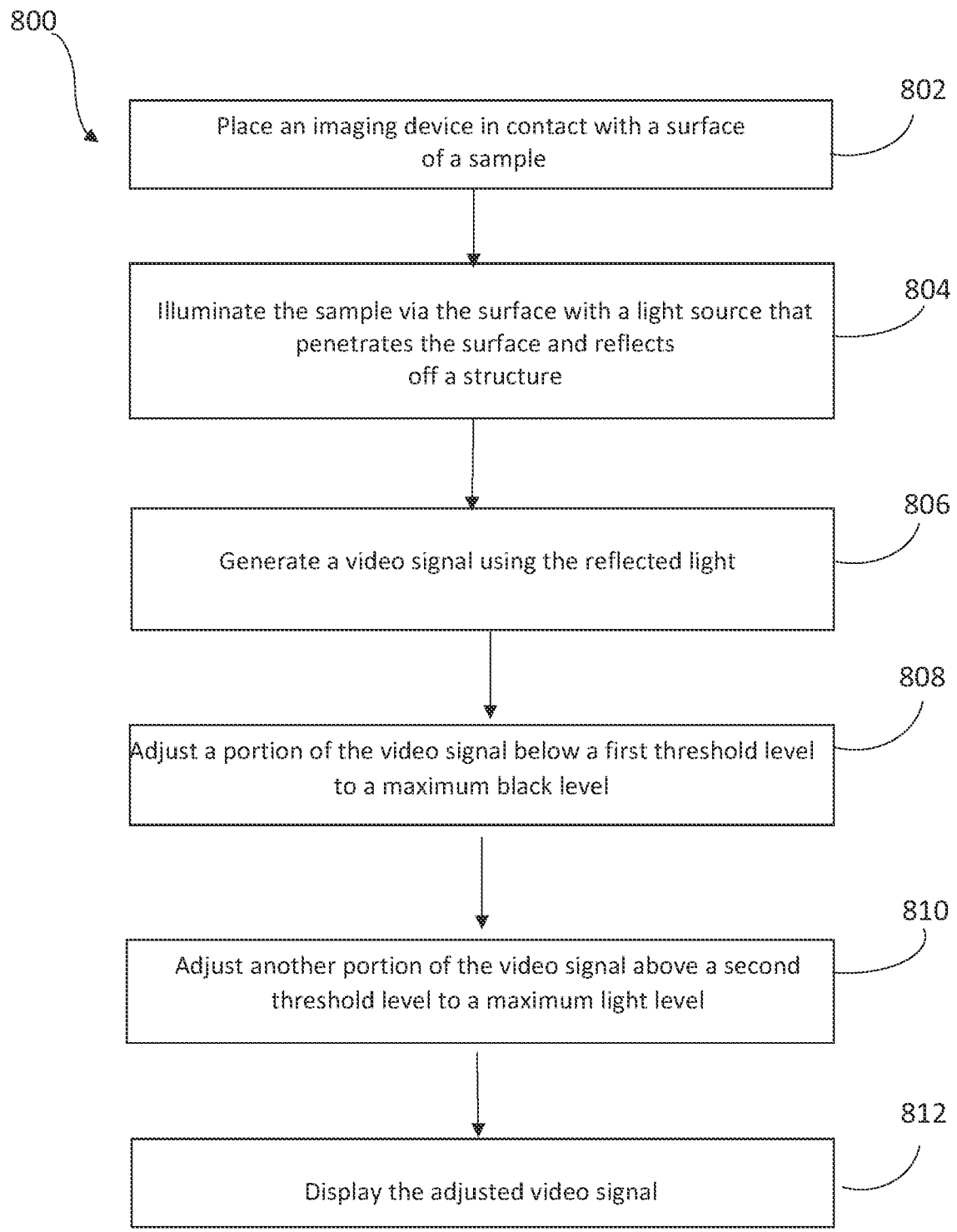
FIG. 8 illustrates a flow diagram of a method of processing a video signal, according an embodiment of the present invention.

Referring now to FIG. 8, a flow diagram of a method 800 of generating and displaying an adjusted video signal is shown, according to an example embodiment. Method 800 may be executed by a user of an imaging system (e.g., the imaging system 600 described with respect to FIG. 6) to generate an image of subsurface features within a sample. For example, method 800 may be performed to image a vein embedded in tissue of a patient.

In an operation 802, an imaging device is placed in contact with a surface of a sample. The imaging device may include a layer of optically transparent material (e.g., such as the optically transparent material 612 described with respect to FIG. 6) configured to be pressed against the surface. In an operation 804, the sample is illuminated via a light source (e.g., the light sources 614) that emits radiation that penetrates the sample's surface (e.g., near infrared light at approximately 940 nm) and scatters off a structure within the sample. In an operation 806, a video signal is generated using the scattered light. For example, the scattered light may be focused via an adjustable focusing element (e.g., the focusing element 616) onto a two-dimensional imaging detector to generate a video signal. Imaging signals generated via the detector may be provided through any suitable connection to a nonlinear processor configured to perform the various operations described herein.

In an operation 808, a portion of the video signal below a first threshold level is adjusted to a maximum black level. For example, a video signal may be provided to the processor 630. In some embodiments, upon receipt of the video signal, the processor 630 may bias the video signal's DC black level via a reference voltage. In certain embodiments, the biasing may be omitted. The biased signal may then undergo maximum value processing where a portion of the video signal (e.g., the back-porch portion or the sync top) is forced to be equal to a black level voltage ("clamped"). The black level voltage may be user-defined via a user input (e.g., via a user input device coupled to the processor). The clamped signal is then compared with the active video portion of the video signal such that active video portion is modified. The modified active video portion is modified such that every portion thereof below the black level voltage is converted to the black level voltage. A difference signal comprising a difference between the modified active video portion and the black level voltage may be taken so as to eliminate all portions of the video signal below the black level voltage.

In some embodiments, when, for example, the video signal is a digital video signal, a processor 630 may execute instructions to determine a black state value for the digital video signal upon receipt of the digital video signal. For example, the black state value may be a predetermined value configured to render a black image on the display 640. The processor 630 may subtract the sum of the black state value and a user-defined value from color or brightness values (e.g., of a bitmapped video frame) of the digital video signal to create a subtracted digital video signal. The brightness values may be determined via any known coefficient system. Negative values in the digital signal after this calculation may then be replaced with a reference value configured to render a dark image on the display 640. This way, the user may define a darkly-displayed color threshold on the screen to only show features reflecting radiation that generates image signals of a certain brightness.

In an operation 810, another portion of the video signal above a second threshold is adjusted to a maximum light level. In some embodiments, the second threshold is equal to the first threshold. For example, the difference signal described herein may be amplified such that the portion of the active video signal above the black level voltage is brightened and more visible in a resultant image. In various embodiments, the user may adjust a multiplier applied via the amplifier so as to adjust the maximum light level. In an operation 812, the adjusted video signal is displayed via a display device attached to the processor.

The various implementations of an adaptive processor described herein can be implemented in hardware, software, or a hybrid implementation. The computer program product can be composed of modules that are in operative communication with one another, and which are designed to pass information or instructions to display. The computer program product can be configured to operate on a general purpose computer, or an application specific integrated circuit ("ASIC").

As described above, prior art subcutaneous vessel imagers use large, multiple, and often separate assemblies with complicated optics to image subcutaneous structures. In contrast, embodiments of the invention may be light-weight, inexpensive, and completely self-contained, may operate as a two- or three-dimensional imager, and may use an adaptive nonlinear processor to increase image contrast.

These features make embodiments of the invention useful for clinicians and field users alike. As staffing costs go up, and as hospitals and clinics strive to lower costs, more and more health professions are being called upon to cross-train. Embodiments of the invention may allow persons who are not trained as phlebotomists to quickly master the skills necessary to access veins. Furthermore, in the battlefield, embodiments of the invention may enable an individual service member to deliver medications or fluids intravenously with a greater possibility of success. The closed headset and the chosen illumination wavelength may combine to enable light discipline on the battlefield. Additionally, during an aircraft or spacecraft mission, intravenous access for drawing blood or infusion could be carried out by under-skilled personnel, thus allowing for a higher level of personnel health mitigation during flight. Finally, sub-surface lesions, especially heavily vascular sub-surface lesions, such as cancers, could be imaged by embodiments of the invention in any modest setting.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

We claim:

1. A method of imaging a structure within a sample, the method comprising:
    placing an imaging device and an illuminator in proximity to the sample such that radiation originating from the illuminator has a propagation path to a surface of the sample;
    irradiating the sample via the illuminator such that at least a portion of the radiation scatters off of the structure towards the imaging device;
    providing the scattered radiation to a detector of the imaging device to generate a digital video signal;
    determining, via a processor communicably coupled to the imaging device, a black state value for the digital video signal;
    subtract, via the processor, a sum of the black state value and a user-defined black level clamp value from the digital video signal to create a subtracted digital video signal;
    setting, via the processor, negative values in the subtracted digital video signal to a reference level to create modified image data;
    amplifying, via the processor, the modified image data by a user-defined gain to create contrast enhanced image data; and
    displaying, via a display device, the contrast enhanced image data to provide an image of the structure.

2. The of claim 1, wherein the imaging device includes a housing in which the detector and a focusing device are disposed, wherein providing the scattered radiation to the detector includes focusing, via the focusing device, the scattered radiation onto the detector.

3. The method of claim 2, wherein the illuminator is attached to the housing.

4. The method of claim 3, wherein the imaging device includes a layer of material transparent to the radiation emitted by the illuminator disposed on an end thereof, wherein placing the imaging device and illuminator in proximity to the sample includes placing the layer of material in direct contact with the surface of the sample.

5. The method of claim 4, wherein the illuminator includes an adjustable light source configured to emit a user-selectable band of radiation between 820 nm and 950 nm.

6. The method of claim 5, wherein the illuminator includes a plurality of light sources disposed in a ring-shaped arrangement centered about an optical axis of the imaging device, wherein the plurality of light sources is disposed between the focusing device and the end.

7. The method of claim 5, wherein the housing includes a window on a side surface thereof, wherein the illuminator is attached to the side surface adjacent to the window, wherein the imaging device further comprises an optical splitter disposed on the optical axis configured to direct a portion of the radiation from the light source along the optical axis towards the sample.

8. The method of claim 7, wherein the layer of material includes a focusing lens configured such that the imaging device is telecentric.

9. The method of claim 5, wherein a position of a focal point of the focusing device is user adjustable to accommodate for a depth of the structure.

10. The method of claim 2, wherein the processor includes a user input device configured to receive user inputs to adjust the black level clamp voltage and the gain after the image of the structure is displayed.

11. The method of claim 1, wherein the processor and display are attached to the imaging device.

12. The method of claim 1, further comprising performing, via the processor, edge enhancement on the contrast enhanced image data.

13. The method of claim 1, wherein the sample comprises biological tissue.

14. The method of claim 1, further comprising:
    generating an additional contrast enhanced video signal via an additional imaging device having a different angle of view of the structure than the imaging device; and
    combining the contrast enhanced video signals into a three-dimensional video signal prior to display.

15. The method of claim 14, wherein the imaging devices are held in relation to one another via an adjustable mounting structure, wherein the relative positioning of the imaging devices is adjustable by a user via supplying a user input to the processor.

16. The method of claim 1, wherein the processor is communicably coupled to a non-transitory computer readable medium storing instructions configured to cause the processor to perform the clamping, combining, removing, and amplifying operations on a digitized version of the video signal.

17. A method of imaging a structure within a sample, the method comprising:
    placing an imaging device in contact with the sample such that radiation originating from an illuminator of the imaging device has a propagation path to a surface of the sample;
    irradiating the sample via the illuminator such that at least a portion of the radiation scatters off of the structure;
    providing the scattered radiation to a detector to generate a digital video signal;
    determining, via a processor communicably coupled to the imaging device, a black state value for the digital video signal;
    subtracting, via the processor, a sum of the black state value and a user-defined black level clamping value from the digital video signal to create subtracted image data;
    substituting, via the processor, negative values in the subtracted image data with a reference value to create modified image data;
    amplifying, via the processor, the modified image data by a user-defined gain to create contrast enhanced image data; and
    displaying, via a display device, the contrast enhanced image data to provide an image of the structure.

18. The method of claim 17, wherein providing the scattering radiation to the detector includes focusing, via a focusing device of the imaging device, the scattered radiation onto the detector.

19. The method of claim 18, wherein the imaging device includes a layer of material transparent to the radiation emitted by the illuminator disposed on an end thereof, wherein placing the imaging device and illuminator in proximity to the sample includes placing the layer of material in direct contact with the surface of the sample.

20. The method of claim 19, wherein the imaging device includes a window on a side surface thereof, wherein the illuminator is attached to the side surface adjacent to the window, wherein the imaging device further comprises an optical splitter disposed on an optical axis configured to direct a portion of the radiation to the light source along the optical axis towards the sample.

* * * * *